US012004721B2

United States Patent
Niijima et al.

(10) Patent No.: US 12,004,721 B2
(45) Date of Patent: Jun. 11, 2024

(54) ENDOSCOPE, PROGRAM, AND INFORMATION PROCESSING METHOD

(71) Applicant: HOYA CORPORATION, Tokyo (JP)

(72) Inventors: Yoshiyuki Niijima, Tokyo (JP); Yoshihiro Hayashi, Tokyo (JP); Yukari Akino, Tokyo (JP); Shinya Shimotashiro, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 116 days.

(21) Appl. No.: 17/795,011

(22) PCT Filed: Jul. 28, 2021

(86) PCT No.: PCT/JP2021/027837
§ 371 (c)(1),
(2) Date: Jul. 25, 2022

(87) PCT Pub. No.: WO2022/064834
PCT Pub. Date: Mar. 31, 2022

(65) Prior Publication Data
US 2023/0089085 A1      Mar. 23, 2023

(30) Foreign Application Priority Data
Sep. 25, 2020   (JP) ................. 2020-160962

(51) Int. Cl.
*A61B 1/06* (2006.01)
*G02B 23/26* (2006.01)
(52) U.S. Cl.
CPC ................ *A61B 1/06* (2013.01); *G02B 23/26* (2013.01)

(58) Field of Classification Search
CPC ....... A61B 1/06; A61B 1/0655; A61B 1/0638; A61B 1/0051; G02B 23/26
(Continued)

(56) References Cited

U.S. PATENT DOCUMENTS

| 2013/0050454 | A1 | 2/2013 | Ogasawara |
| 2014/0081083 | A1* | 3/2014 | Morita ............... A61B 1/00177 600/109 |

(Continued)

FOREIGN PATENT DOCUMENTS

| JP | 2003-116783 A | 4/2003 |
| JP | 2012-139435 A | 7/2012 |

(Continued)

OTHER PUBLICATIONS

International Search Report issued in International Bureau of WIPO Patent Application No. PCT/JP2021/027837, dated Oct. 19, 2021, along with an English translation thereof.

*Primary Examiner* — Sherrie Hsia
(74) *Attorney, Agent, or Firm* — GREENBLUM & BERNSTEIN, P.L.C.

(57) ABSTRACT

A light amount control unit of an endoscope derives a photometric value in an area of an observation spot corresponding to each of angular ranges of a first light output unit and a second light output unit having different wavelength ranges based on imaging data about the observation spot output from an imaging unit, derives an amount of light from each of the first light output unit and the second light output unit based on the derived photometric value, and causes each of the first light output unit and the second light output unit to output illumination light based on the derived amount of light.

10 Claims, 8 Drawing Sheets

(58) Field of Classification Search
USPC .................................................. 348/65, 45
See application file for complete search history.

(56) References Cited

U.S. PATENT DOCUMENTS

2016/0073853 A1    3/2016   Venkatesan et al.
2016/0345811 A1   12/2016   Sone et al.

FOREIGN PATENT DOCUMENTS

| JP | 5132841 B2    | 1/2013  |
| JP | 2014-230708 A | 12/2014 |
| JP | 2015-16021 A  | 1/2015  |
| JP | 5942063 B1    | 6/2016  |
| JP | 2016-128024 A | 7/2016  |

* cited by examiner

| PHOTOMETRIC VALUE | OBSERVATION MODE (TYPE OF LED) | AMOUNT OF LIGHT (WHITE MODE) | AMOUNT OF LIGHT (NARROWBAND MODE) |
|---|---|---|---|
| xxx01 TO xxx02 | WHITE MODE | ww01 | null |
| xxx03 TO xxx04 | WHITE MODE | ww02 | null |
| xxx05 TO xxx06 | WHITE MODE | ww03 | null |
| xxx07 TO xxx08 | WHITE MODE | ww04 | null |
| ... | WHITE MODE | ... | null |
| yyy01 TO yyy02 | NARROWBAND MODE | null | kk01 |
| yyy03 TO yyy04 | NARROWBAND MODE | null | kk02 |
| yyy05 TO yyy06 | NARROWBAND MODE | null | kk03 |
| yyy07 TO yyy08 | NARROWBAND MODE | null | kk04 |
| ... | NARROWBAND MODE | null | ... |

ENDOSCOPE, PROGRAM, AND INFORMATION PROCESSING METHOD

TECHNICAL FIELD

The present technology relates to an endoscope, a program, and an information processing method.

The present application claims priority based on Japanese Patent Application No. 2020-160962 filed on Sep. 25, 2020, the entire contents of which are incorporated herein by reference.

BACKGROUND ART

An endoscope is a medical instrument to be inserted into a body cavity of a subject to observe and treat a desired site, and includes an imaging unit provided in a distal tip of an insertion tube to be inserted into the body cavity, and an illumination device illuminating an imaging field of view of the imaging unit. Patent Literature 1 discloses an endoscope including an illumination device for achieving illumination in a wide angular range of 180° or more to enable observation at a wide viewing angle.

In recent years, endoscopes enabling image-enhanced observation under illumination of narrowband light (purple light, green light, or the like) as well as observation under white light have also been widely used, and Patent Literature 2 discloses an endoscope device that acquires an image by alternately emitting white light and narrowband light.

CITATION LIST

Patent Literature

Patent Literature 1: JP 2015-16021 A
Patent Literature 2: JP 2016-128024 A

SUMMARY OF INVENTION

Technical Problem

However, the endoscope device described in Patent Literature 2 has a problem that dimming according to a photometric value for each of the white light and the narrowband light is not considered.

In one aspect, an object of the present disclosure is to provide an endoscope or the like capable of performing dimming according to a photometric value of illumination light in each of different wavelength ranges.

Solution to Problem

In one aspect of the present disclosure, an endoscope includes: an imaging unit provided in a distal tip of an insertion tube to image an observation spot via an objective lens; a first light output unit disposed around the objective lens to output first illumination light for illuminating the observation spot; a second light output unit disposed around the objective lens to output second illumination light for illuminating the observation spot in a wavelength range wider than that of the first illumination light in an angular range larger than that of the first light output unit; and a light amount control unit controlling an amount of light output from each of the first light output unit and the second light output unit, in which the light amount control unit: derives a photometric value in an area of the observation spot corresponding to each of the angular ranges of the first light output unit and the second light output unit based on imaging data about the observation spot output from the imaging unit; derives the amount of light from each of the first light output unit and the second light output unit based on the derived photometric value; and causes each of the first light output unit and the second light output unit to output illumination light based on the derived amount of light.

In another aspect of the present disclosure, a program causes a computer to execute the following processing, the computer controlling an amount of light output from each of a first light output unit disposed around an objective lens to output first illumination light for illuminating an observation spot, and a second light output unit disposed around the objective lens to output second illumination light for illuminating the observation spot in a wavelength range wider than that of the first illumination light in an angular range larger than that of the first light output unit: deriving a photometric value in an area of the observation spot corresponding to an angular range of each of the first light output unit and the second light output unit based on imaging data about the observation spot output from an imaging unit imaging the observation spot via the objective lens; deriving the amount of light from each of the first light output unit and the second light output unit based on the derived photometric value; and causing each of the first light output unit and the second light output unit to output illumination light based on the derived amount of light.

In another aspect of the present disclosure, an information processing method performed by a computer controlling an amount of light output from each of a first light output unit disposed around an objective lens to output first illumination light for illuminating an observation spot, and a second light output unit disposed around the objective lens to output second illumination light for illuminating the observation spot in a wavelength range wider than that of the first illumination light in an angular range larger than that of the first light output unit includes the following steps: deriving a photometric value in an area of the observation spot corresponding to an angular range of each of the first light output unit and the second light output unit based on imaging data about the observation spot output from an imaging unit imaging the observation spot via the objective lens; deriving the amount of light from each of the first light output unit and the second light output unit based on the derived photometric value; and causing each of the first light output unit and the second light output unit to output illumination light based on the derived amount of light.

Advantageous Effects of Invention

According to the present disclosure, it is possible to provide an endoscope or the like that performs dimming according to a photometric value of illumination light in each of different wavelength ranges.

DESCRIPTION OF EMBODIMENTS

First Embodiment

Figure 1:
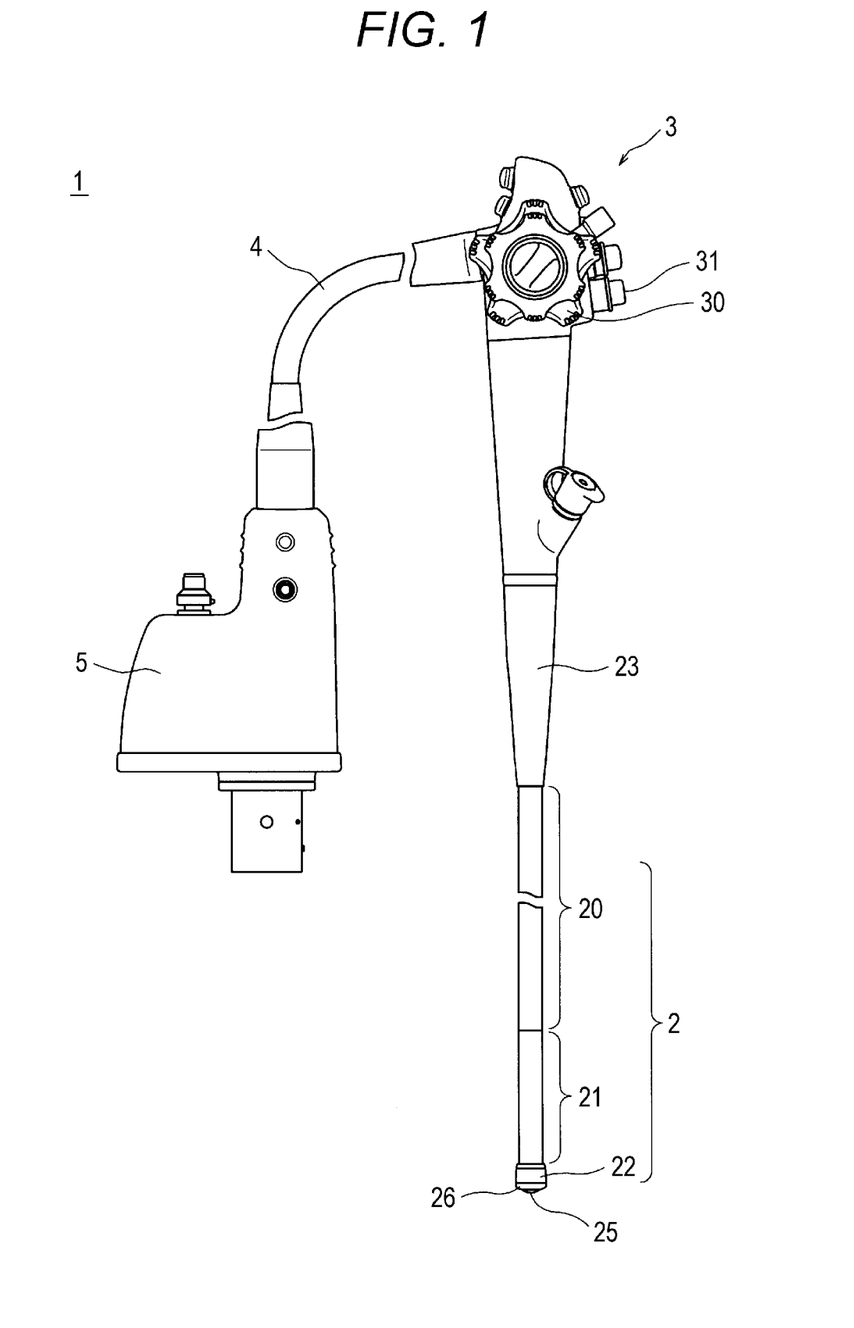
FIG. 1 is an exterior view of an endoscope according to a first embodiment.

Hereinafter, the present invention will be described in detail with reference to the drawings illustrating embodiments of the present invention. FIG. 1 is an exterior view of an endoscope 1 according to a first embodiment. The endoscope 1 includes an insertion tube 2, an operation unit 3, a universal tube 4, and a connector unit 5. The insertion tube 2 is a portion to be inserted into a body cavity, and includes a long soft portion 20 and a distal tip 22 connected to one end of the soft portion 20 via a bending section 21. The other end of the soft portion 20 is connected to the operation unit 3 via a cylindrical connection portion 23. The universal tube 4 has one end connected to the operation unit 3 and extends in a direction different from the insertion tube 2, and the connector unit 5 is connected to the other end of the universal tube 4.

The operation unit 3 is provided to be gripped by a user (operator) of the endoscope 1 such as a doctor to perform various operations, and includes a bending operation knob 30 and a plurality of operation buttons 31 or the like. The bending operation knob 30 is connected to the bending section 21 by a wire (not illustrated) passing through the inside of each of the connection portion 23 and the soft portion 20. The bending section 21 is bent in two directions orthogonal to each other in an axial cross section by operating the bending operation knob 30, thereby changing a direction of the distal tip 22 inserted into the body cavity.

Figure 2:
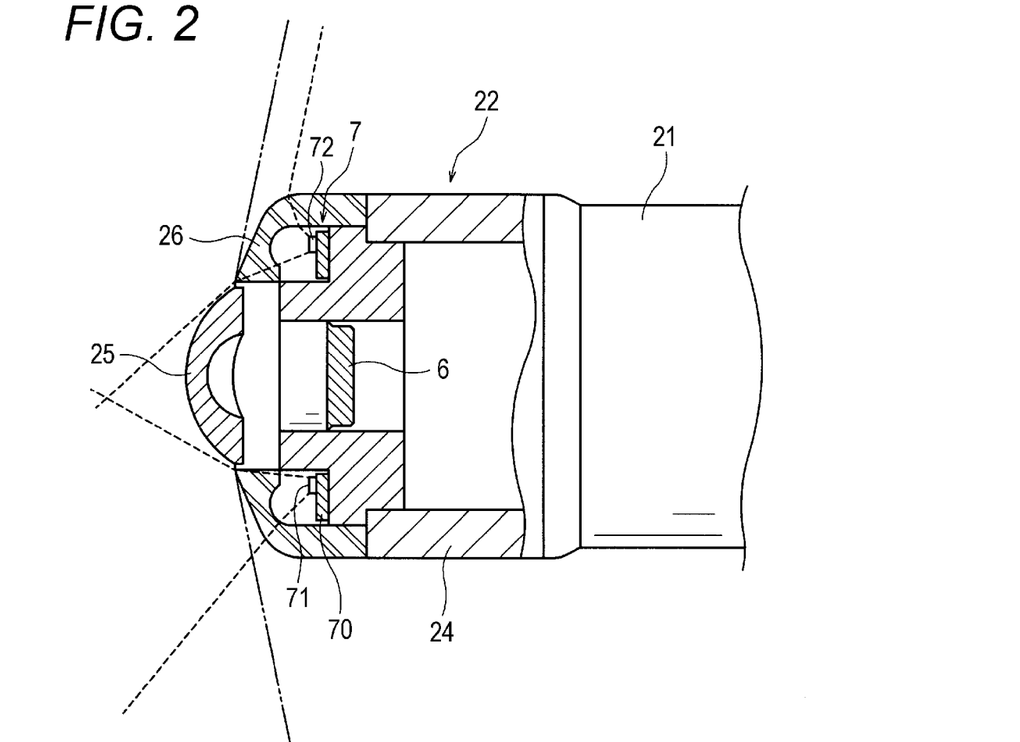
FIG. 2 is an enlarged view of a distal tip of an insertion tube.
Figure 3:
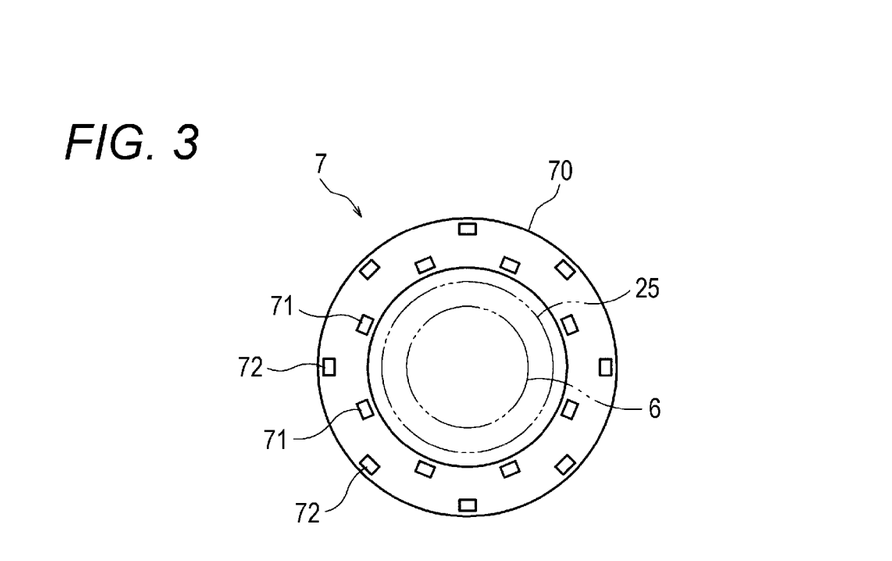
FIG. 3 is a plan view illustrating an example of how first LEDs (narrowband light LEDs) and second LEDs (white LEDs) are arranged.

FIG. 2 is an enlarged view of the distal tip 22 of the insertion tube 2. FIG. 3 is a plan view illustrating an example of how first LEDs 71 (narrowband light LEDs) and second LEDs 72 (white LEDs) are arranged. The distal tip 22 includes a cylindrical housing 24 of which one side is fixed to the bending section 21. The other side of the housing 24 is covered with a central objective lens 25 and an annular light distribution lens 26 surrounding the periphery of the objective lens 25. An imaging unit 6 is provided inside the housing 24 to face an inner side of the objective lens 25. That is, the imaging unit 6 images a subject to be observed (an object), which is a body part such as a body cavity, through the objective lens 25. The objective lens 25 is fitted into an inner frame of a hole provided in the distal tip 22 of the insertion tube 2 and functions as an observation window. An illumination unit 7 is provided to face an inner side of the light distribution lens 26.

The imaging unit 6 includes an image sensor such as a complementary metal oxide semiconductor (CMOS) and an optical system for forming an image on an imaging surface of the image sensor, and images the inside of the body cavity through the objective lens 25. The objective lens 25 is, for example, a wide-angle lens, and the imaging unit 6 is configured to capture an image at a viewing angle of 180° or more by setting the optical system including the objective lens 25. A two-dot chain line in FIG. 2 indicates an imaging field of view of the imaging unit 6. The imaging unit 6 outputs imaging data (image signal) of the subject to be observed (object) that has been imaged to a reception circuit 61. The imaging data (image signal) output from the imaging unit 6 is subjected to preprocessing such as AD conversion or white balance correction in the reception circuit 61 and a gain circuit 62, and the preprocessed imaging data is output to a signal processing circuit 12 of a processor device 10.

The illumination unit 7 includes an annular substrate 70 surrounding the periphery of the imaging unit 6, and first LEDs 71 (narrowband LEDs) and second LEDs 72 (white LEDs) mounted on one surface of the substrate 70 facing the light distribution lens 26. A plurality of (eight in the drawing) first LEDs 71 and a plurality of (eight in the drawing) second LEDs 72 are provided, the first LEDs 71 being arranged at substantially equal intervals on an inner circumferential side (the side close to the imaging unit 6) of the annular substrate 70, and the second LEDs 72 being arranged at substantially equal intervals outside a region where the first LEDs 71 are arranged. In FIG. 3, positions of the imaging unit 6 and the objective lens 25 are indicated by two-dot chain lines.

A cross section of the first LED 71 at an arrangement position thereof is illustrated in the lower half of FIG. 2, and a cross section of the second LED 72 at an arrangement position thereof in the upper half of FIG. 2. The light distribution lens 26 is a cylindrical lens having such a shape as to extend outward from a peripheral edge portion of the objective lens 25 and be continuous up to a peripheral wall of the housing 24 through a bending portion thereof, and light emitted from the first LEDs 71 or the second LEDs 72 is irradiated through the light distribution lens 26 and illuminates an imaging field of view of the imaging unit 6.

Broken lines in FIG. 2 indicate light distribution ranges of the first LED 71 (narrowband LED) and the second LED 72 (white LED). The light emitted from the first LEDs 71 located inside is incident on a spread portion of the light distribution lens 26, and is intensively distributed to a central portion of the imaging field of view of the imaging unit 6. On the other hand, the light emitted from the second LEDs 72 located outside is incident on the light distribution lens 26 in a wide range from the spread portion to the bending portion thereof to greatly spread, and is distributed to the entire imaging field of view of the imaging unit 6. Note that a concave portion is provided in the vicinity of the bending portion on an inner surface of the light distribution lens 26. The concave portion acts to cause the second LEDs 72 to be irradiated in such a manner that light is distributed in a wider range than the first LEDs 71. In other words, a range in which light is irradiated by the second LEDs 72 is wider than that by the first LEDs 71. That is, the light distribution characteristics of the first LEDs 71 (narrowband LEDs) and the second LEDs 72 (white LEDs) are different based on the wavelength ranges (spectral bandwidths) of the first LEDs 71 (narrowband LEDs) and the second LEDs 72 (white LEDs). The first LEDs 71 and the second LEDs 72 are arranged so that an irradiation range of the first LEDs 71 (narrowband LEDs) having a narrow wavelength range is narrower than an irradiation range of the second LEDs 72 (white LEDs) having a wide wavelength range.

The first LEDs 71 (narrowband LEDs) emits narrowband light including light in violet and green wavelength ranges. For example, four of the eight first LEDs 71 are green LED chips that emit green light, and the other four first LEDs 71 are violet LED chips that emit ultraviolet light, the green LED chips and the violet LED chips being alternatively located. These eight first LEDs 71 and the light distribution lens 26 constitute a first light output unit that outputs narrowband light.

The second LEDs 72 are white LEDs that emit white light, and are configured by, for example, covering light emitting surfaces of blue LED chips that emit blue light with a yellow phosphor. The second LEDs 72 and the light distribution lens 26 constitute a second light output unit that outputs white light. The first and second LEDs 71 and 72 may be other types of light emitting elements such as LDs.

An image is captured by the imaging unit 6 under illumination with the narrowband light output from the first light output unit or the white light output from the second light output unit. A light distribution angle of the white light is larger than a light distribution angle of the narrowband light, preferably almost equal to a viewing angle of the imaging unit 6, and more preferably equal to or larger than the viewing angle of the imaging unit 6. Then, an image can be captured under light in a sufficient amount in the entire field of view. Although the spectrum of the narrowband light is limited, since the light distribution angle of the narrowband light is smaller than the light distribution angle of the white light, the light distribution range of the narrowband light is smaller (narrower) than the light distribution range of the white light. Therefore, concerning an amount of light (photometric amount) per unit area in the light distribution range, an image can be captured under the same amount of light in the light distribution range of the narrowband light and in the light distribution range of the white light.

As described above, the first LEDs 71 (narrowband LEDs) and the second LEDs 72 (white LEDs) are provided along a circumference of the objective lens 25. The second LEDs 72 (white LEDs) are provided to be further away from the objective lens 25 in an outward direction (on a side closer to the outer circumference) than the first LEDs 71 (narrowband LEDs), and thus, a circle formed by arranging the second LEDs 72 (white LEDs) is larger than a circle formed by arranging the first LEDs 71 (narrowband LEDs). The first LEDs 71 and the second LEDs 72 are arranged in respectively corresponding ones of a plurality of areas segmented in an image captured by the imaging unit 6. In a case where the image captured by the imaging unit 6 is divided into four areas, for example, based on vertical and horizontal directions, the first LEDs 71 and the second LEDs 72 are arranged in respectively corresponding ones of the four divided areas.

As illustrated in the drawing in the present embodiment, in a case where eight first LEDs 71 and eight second LEDs 72 are provided, LEDs (two first LEDs 71 and two second LEDs 72) of which main light distribution range is an upper right area (area 1) of the image are disposed in a range of 0° or more and less than 45° with respect to the central angle. In addition, LEDs (two first LEDs 71 and two second LEDs 72) of which main light distribution range is a lower right area (area 4) of the image are disposed in a range of 45° or more and less than 90° with respect to the central angle. In addition, LEDs (two first LEDs 71 and two second LEDs 72) of which main light distribution range is a lower left area (area 3) of the image are disposed in a range of 90° or more and less than 270° with respect to the central angle. In addition, LEDs (two first LEDs 71 and two second LEDs 72) of which main light distribution range is an upper left area (area 2) of the image are disposed in a range of 270° or more and less than 360° with respect to the central angle. By providing an individual first LED 71 and an individual second LED 72 to correspond to each of a plurality of areas into which an image captured by the imaging unit 6 is divided as described above, light amounts of the individual first LED 71 and the individual second LED 72 corresponding to each of these areas can be derived based on a photometric value in each area. Then, the individual first LEDs 71 and the individual second LEDs 72 can be controlled to emit light in different amounts in the individual areas. In the present embodiment, when the image captured by the imaging unit 6 is segmented (divided) into a plurality of areas, the number of segments (the number of divisions) is four, but is not limited thereto. The number of a plurality of areas (the number of divisions) into which the image is segmented may be the same (eight in the present embodiment) as the number of first LEDs 71 and the number of second LEDs 72. By setting the number of segments (the number of divisions) according to the number of first LEDs 71 and the number of second LEDs 72, it is possible to control the individual first LEDs 71 and the individual second LEDs 72 more finely to emit light in different amounts in the individual areas. In the present embodiment, when the image captured by the imaging unit 6 is segmented (divided) into a plurality of areas, the number of segments (the number of divisions) is the same (four in the present embodiment) as the number of segments into which the first LEDs 71 (narrowband LEDs) are classified and the number of segments into which the second LEDs 72 (white LEDs) are classified, but is not limited thereto. The number of segments into which the first LEDs 71 (narrowband LEDs) are classified may be different from the number of segments into which the second LEDs 72 (white LEDs) are classified. For example, the number of segments into which the second LEDs 72 (white LEDs) are classified may be eight, and the number of segments into which the first LEDs 71 (narrowband LEDs) are classified may be four, such that the number of segments into which the second LEDs 72 (white LEDs) irradiating light in a wide range are classified is larger than the number of segments into which the first LEDs 71 (narrowband LEDs) irradiating light in a narrow range.

Figure 4:
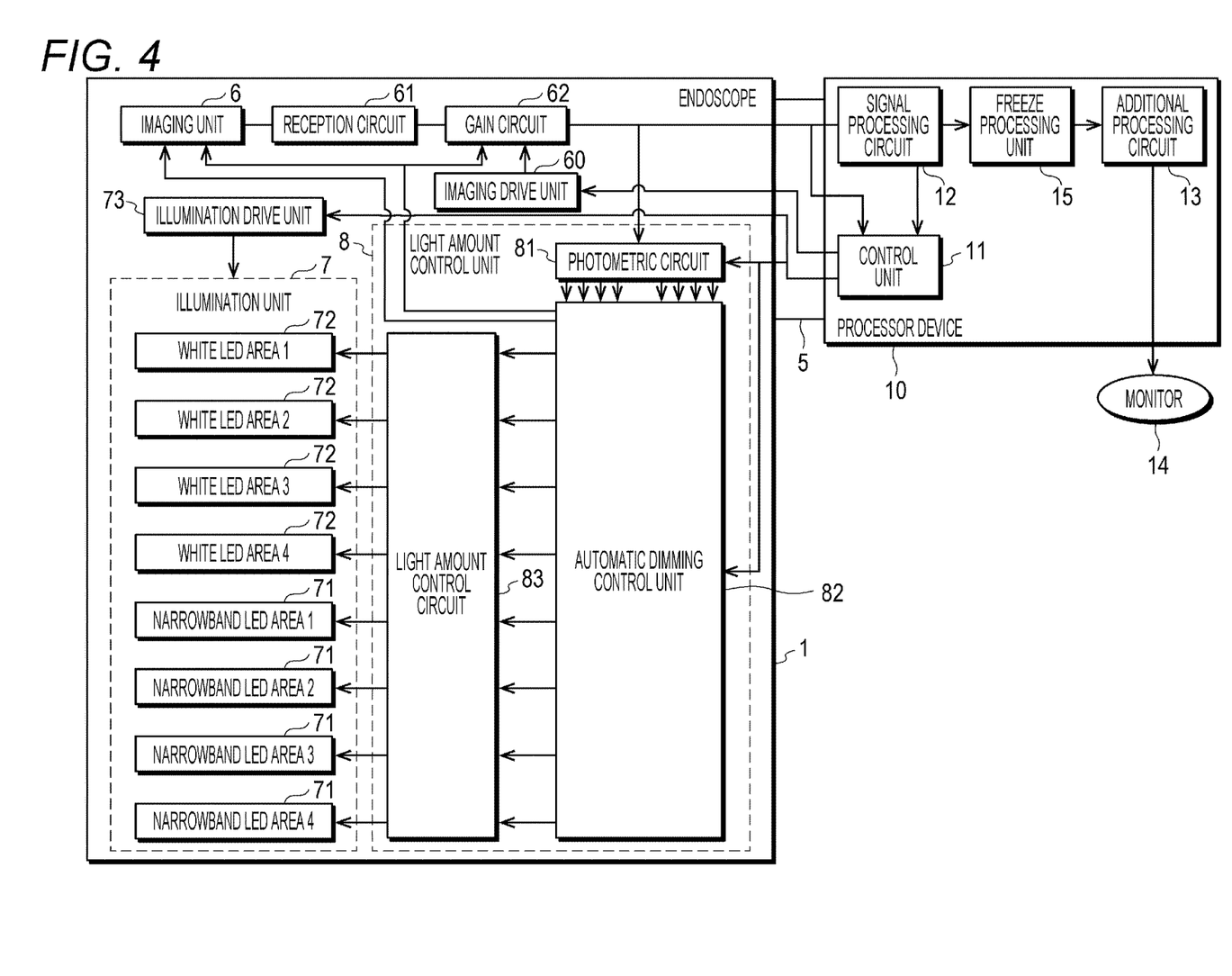
FIG. 4 is a block diagram of an endoscope device.
Figure 5:
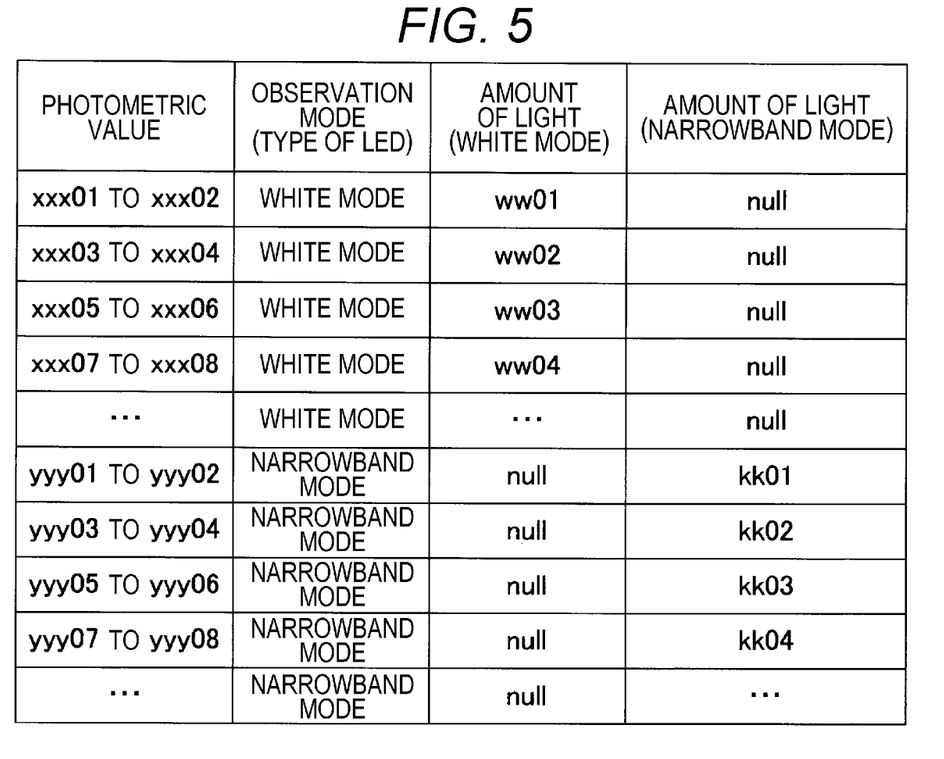
FIG. 5 is an explanatory diagram illustrating an example of a look-up lock up table for deriving an amount of light.

FIG. 4 is a block diagram of an endoscope 1 device. FIG. 5 is an explanatory diagram illustrating an example of a look-up table for deriving an amount of light. The endoscope 1 is connected to the processor device 10 via the connector unit 5, and is used as an endoscope 1 device. The processor device 10 includes a control unit 11, a signal processing circuit 12, a freeze processing unit 15 that performs still image processing, an additional processing circuit 13, etc. The control unit 11, the signal processing circuit 12, the freeze processing unit 15, and the additional processing circuit 13 are communicably connected to each other by an internal bus. The control unit 11 includes a CPU, a ROM, and a RAM, and integrally controls the endoscope 1 device by operating the CPU according to a control program stored in the ROM.

The endoscope 1 includes an imaging drive unit 60 that drives the imaging unit 6 and an illumination drive unit 73 that drives the illumination unit 7. The imaging drive unit 60 drives the imaging unit 6 in a rolling shutter type according to a control command given from the control unit 11. An output signal of the imaging drive unit 60 is given to the gain circuit 62 in a unit of one frame through the reception circuit 61, and predetermined preprocessing, such as white balance processing, is performed to output imaging data (an image signal) to the signal processing circuit 12 of the processor device 10. For the preprocessing of the gain circuit 62, a gain value given from the imaging drive unit 60 is used.

The illumination drive unit 73 drives the illumination unit 7 according to a control command given from the control unit 11 to cause the first LEDs 71 and the second LEDs 72 to selectively or alternately emit light. An imaging operation of the imaging unit 6 is executed in synchronization with the driving of the illumination unit 7, and an image output obtained under illumination of the narrowband light by the first LEDs 71 or under illumination of the white light by the second LEDs 72 is continuously or alternately input to the signal processing circuit 12. An operation mode of the illumination unit 7 can be selected by operating the operation button 31 provided on the operation unit 3. That is, the operation mode of the illumination unit 7 includes an observation mode (white mode) using the second LEDs 72 (white LEDs) or an observation mode (narrowband mode) using the first LEDs 71 (narrowband LEDs).

The signal processing circuit 12 performs image processing, such as gamma correction and interpolation processing, on the input imaging data (image signal), and outputs the processed imaging data to the additional processing circuit 13. The signal processing circuit 12 may output the input image subjected to the image processing to the additional processing circuit 13 via the freeze processing unit 15 that performs still image processing. The freeze processing unit 15 may perform still image processing, for example, using a double date rate random access memory (DDR RAM) as a buffer area.

The additional processing circuit 13 performs mask processing on the peripheral edge portion, performs zoom processing on an image under narrowband light, further converts the image into an image conforming to a predetermined standard by superimposition processing of various characters and images, and outputs the converted image to an external monitor 14. Note that an area to be subjected to the mask processing in the image under narrowband light may be expanded by performing zoom processing. The monitor 14 is a display device such as a liquid crystal display or an organic EL display, and displays an image captured by the imaging unit 6 based on an image signal output from the processor device 10. The user of the endoscope 1 can observe a desired site in the body cavity through the display of the monitor 14 under illumination of narrowband light or white light.

The endoscope 1 further includes a light amount control unit 8 including a photometric circuit 81, an automatic dimming control unit 82, and a light amount control circuit 83. Similarly to the first LEDs 71 (narrowband LEDs) and the second LEDs 72 (white LEDs), the light amount control unit 8 may be mounted on the substrate 70.

The light amount control unit 8 is communicably connected to the gain circuit 62 and the like by a branch bus branched from the internal bus connecting the gain circuit 62 and the signal processing circuit 12 of the processor device 10 to each other. The light amount control unit 8 may further be communicably connected to the control unit 11 of the processor device 10 via the internal bus. The light amount control unit 8 acquires the imaging data (image signal) output from the gain circuit 62, and derives a photometric value at an observation spot based on the acquired imaging data. The light amount control unit 8 derives amounts of light from the first LEDs 71 (narrowband LEDs) and the second LEDs 72 (white LEDs) based on the photometric value, and controls the amounts of light from the first LEDs 71 and the second LEDs 72 based on the derived amounts of light.

The photometric value is derived by the photometric circuit 81. The photometric circuit 81 is constituted by, for example, an FPGA, an ASIC, or the like, and derives a photometric value in a photometric area corresponding to each of the first LEDs 71 (narrowband LEDs) and the second LEDs 72 (white LEDs) in the imaging data (image signal) output from the gain circuit 62. As described above, the irradiation range (light distribution range) of the first LEDs 71 (narrowband LEDs) is different from the irradiation range (light distribution range) of the second LEDs 72 (white LEDs). These irradiation ranges (light distribution ranges) are equivalent to (correspond to) respective photometric areas of the first LEDs 71 (narrowband LEDs) and the second LEDs 72 (white LEDs). Since the irradiation range of the first LEDs 71 (narrowband LEDs) is smaller (narrower) than the irradiation range of the second LEDs 72 (white LEDs), the photometric area (first photometric area) of the first LEDs 71 is smaller (narrower) than the photometric area (second photometric area) of the second LEDs 72.

Area information for specifying the photometric area (first photometric area) of the first LEDs 71 and the photometric area (second photometric area) of the second LEDs 72 is stored in, for example, a memory such as a RAM included in the FPGA or the like constituting the photometric circuit 81. The area information regarding the photometric areas may be defined according to a range based on image coordinate system, a range based on pixel number, or the like in an image captured by the imaging unit 6. In a case where the imaging data (image signal) output from the gain circuit 62 is data in an array format, the area information regarding the photometric areas may be defined according to a range based on array number.

The photometric circuit 81 specifies a photometric area (first photometric area) of the first LEDs 71 or a photometric area (second photometric area) of the second LEDs 72 based on an observation mode. The photometric circuit 81 is operated in conjunction with the illumination drive unit 73 that drives the first LEDs 71 and the second LEDs 72 based on an observation mode, thereby making it possible to acquire the observation mode. That is, similarly to the illumination drive unit 73, the photometric circuit 81 specifies whether the observation mode is a white mode using the second LEDs 72 (white LEDs) or a narrowband mode using the first LEDs 71 (narrowband LEDs) based on a control command given from the control unit 11 of the processor device 10. When the observation mode is a white mode, the photometric circuit 81 acquires area information regarding the photometric area (second photometric area) of the second LEDs 72 (white LEDs). When the observation mode is a narrowband mode, the photometric circuit 81 acquires area information regarding the photometric area (first photometric area) of the first LEDs 71 (narrowband LEDs).

In any observation mode, the outside of the irradiation is not an area where an observation spot is clearly projected, because it has a low exposure and is shown in dark brown on the screen. In this regard, since a photometric value is derived in the irradiation range (photometric area) corresponding to each of the first LEDs 71 (narrowband LEDs) and the second LEDs 72 (white LEDs) having different light distribution characteristics, an area (a dark brown area caused by low exposure) outside the irradiation range (photometric area) can be excluded from an area for deriving the photometric value in any case. Therefore, an appropriate photometric value can be derived according to the irradiation ranges (light distribution characteristics) of the first LEDs 71 (narrowband LEDs) and the second LEDs 72 (white LEDs) having different light distribution characteristics.

When deriving a photometric value in each of these photometric areas, the photometric circuit 81 may derive an average value (average photometric value) of photometric values in the entire photometric area. By deriving the average photometric value, it is possible to control brightness to be constant in an entire image (endoscopic image). Alternatively, the photometric circuit 81 may derive a largest value (peak photometric value) of photometric values in the entire photometric area. By deriving the peak photometric value, it is possible to control brightness to be constant in a bright portion of an image (endoscopic image).

In a case where an image captured by the imaging unit 6 is segmented into a plurality of areas, for example, four areas (Areas 1 to 4) based on vertical and horizontal directions, that is, in a case where an observation spot includes a plurality of divided areas, the photometric circuit 81 may derive a photometric value for each of the plurality of divided areas. In this case, the photometric circuit 81 derives four photometric values, i.e. a photometric value in an upper right photometric area, a photometric value in a lower right photometric area, a photometric value in a lower left photometric area, and a photometric value in an upper left photometric area, according to each observation mode (white mode or narrowband mode). Since the individual LEDs including the first LEDs 71 (narrowband LEDs) and the second LEDs 72 (white LEDs) are arranged in respectively corresponding ones of the plurality of segmented areas, a photometric value for each of the plurality of segmented areas can be used to derive an amount of light from each of these individual LEDs. Therefore, in any observation mode (white mode or narrowband mode), it is possible to appropriately derive amounts of light from LEDs (first LED 71 and second LED 72) corresponding to any one of a plurality of segmented areas, for example, an area where halation or the like occurs, thereby irradiating light in an appropriate amount for each of the individually segmented areas.

The automatic dimming control unit 82 is constituted by, for example, a microcomputer, and derives amounts of light from the first LEDs 71 (narrowband LEDs) and the second LEDs 72 (white LEDs) based on photometric values output from the photometric circuit 81. When the photometric value for each of the plurality of segmented areas is output from the photometric circuit 81, an amount of light from each of the LEDs including the first LEDs 71 (narrowband LEDs) and the second LEDs 72 (white LEDs) provided in respectively corresponding ones of the plurality of areas is derived based on the photometric value for each of the plurality of areas.

In a memory such as a RAM included in the microcomputer or the like constituting the automatic dimming control unit 82, a lookup table for deriving an amount of light based on the photometric value is stored in advance. In the look-up table, for example, amounts of light from the first LEDs 71 (narrowband LEDs) and the second LEDs 72 (white LEDs) are defined to correspond to a photometric value range according to the observation mode. The parameter for the amount of light defined in the lookup table is determined as, for example, a product specification based on the sensitivity characteristic of the imaging unit 6, the light emitting characteristics of the first LEDs 71 (narrowband LEDs) and the second LEDs 72 (white LEDs), or the like.

Referring to a lookup table stored in, for example, a memory included in the microcomputer constituting the automatic dimming control unit 82, the automatic dimming control unit 82 derives an amount of light from each of the individual LEDs including the first LEDs 71 (narrowband LEDs) and the second LEDs 72 (white LEDs) provided in respectively corresponding ones of the plurality of segmented areas based on the photometric value for each of the plurality of segmented areas. The automatic dimming control unit 82 derives amounts of light from either the first LEDs 71 (narrowband LEDs) or the second LEDs 72 (white LEDs) according to the light emission mode. That is, when the light emission mode is a white mode, the automatic dimming control unit 82 derives amounts of light from the second LEDs 72 (white LEDs). When the light emission mode is a narrowband mode, the automatic dimming control unit 82 derives amounts of light from the first LEDs 71 (narrowband LEDs).

The automatic dimming control unit 82 outputs information or a signal regarding the derived amounts of light to the light amount control circuit 83. The information regarding the amounts of light may include, for example, values of LED currents flowing through the first LEDs 71 (narrowband LEDs) and the second LEDs 72 (white LEDs).

The light amount control circuit 83 is constituted by, for example, an FPGA or an ASIC, and is electrically connected to the first LEDs 71 (narrowband LEDs) and the second LEDs 72 (white LEDs) by electric wires, lands on the substrate 70, or the like. The light amount control circuit 83 causes currents to flow through the first LEDs 71 (narrowband LEDs) and the second LEDs 72 (white LEDs) based on the information or signal regarding the amounts of light such as LED current values output from the automatic dimming control unit 82. As a result, it is possible to output illumination light in an appropriate amount to each of the individual LEDs including the first LEDs 71 (narrowband LEDs) and the second LEDs 72 (white LEDs) arranged to correspond to the plurality of segmented areas.

In the present embodiment, the light amount control unit 8 includes a photometric circuit 81 and a light amount control circuit 83 constituted by HW processing units such as FPGAs or ASCIs, and an automatic dimming control unit 82 constituted by an SW processing unit such as a microcomputer, but is not limited thereto. The photometric circuit 81, the automatic dimming control unit 82, and the light amount control circuit 83 included in the light amount control unit 8 may be integrally constituted by, for example, a system-on-a-chip (SoC) or the like. In the present embodiment, the light amount control unit 8 and the illumination drive unit 73 are described as separate functional modules, but are not limited thereto. The light amount control unit 8 and the illumination drive unit 73 that perform control related to the illumination unit 7 may be constituted by an integrated functional module such as an SoC.

Figure 6:
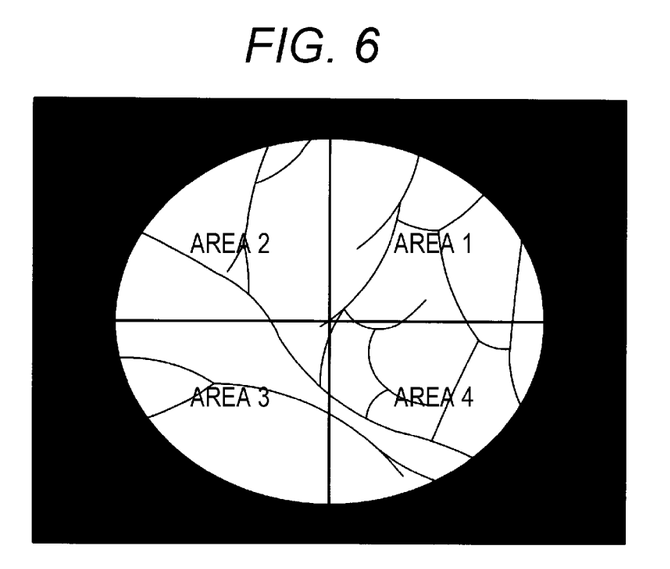
FIG. 6 is an explanatory diagram illustrating an observation spot (photometric area) when illustrated by a first light output unit (narrowband LEDs).
Figure 7:
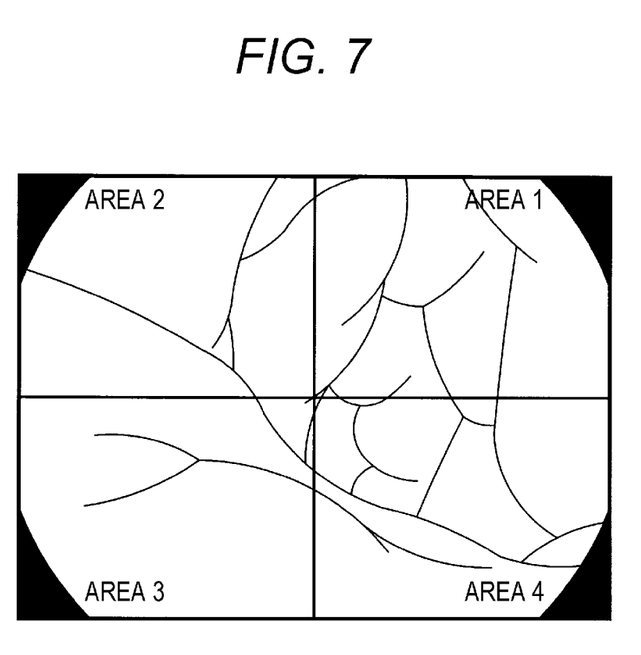
FIG. 7 is an explanatory diagram illustrating an observation spot (photometric area) when illuminated by a second light output unit (white LEDs).

FIG. 6 is an explanatory diagram illustrating an observation spot (photometric area) when illustrated by the first light output unit (narrowband LEDs). FIG. 7 is an explanatory diagram illustrating an observation spot (photometric area) when illuminated by the second light output unit (white LEDs).

As illustrated in the present embodiment, the observation spot (photometric area) when illuminated by the first light output unit (narrowband LEDs) is smaller (narrower) than the observation spot (photometric area) when illuminated by the second light output unit (white LEDs). Such a phenomenon occurs when the light distribution range of the first LEDs 71 (narrowband LEDs) is smaller (narrower) than the light distribution range of the second LEDs 72 (white LEDs).

In a case where the same photometric areas are set for the first light output unit (narrowband LEDs) and the second light output unit (white LEDs) having different light distribution characteristics as described above, there is a concern that either the narrowband LEDs nor the white LEDs may have a significant difference between the photometric area and the light distribution range, making it difficult to derive an appropriate photometric value. In this regard, by using different photometric areas according to the light distribution characteristics of the first light output unit (narrowband LEDs) and the second light output unit (white LEDs), it is possible to appropriately derive a photometric value in any observation mode to perform automatic dimming control for optimizing amounts of light from the first light output unit (narrowband LEDs) and the second light output unit (white LEDs).

Figure 8:
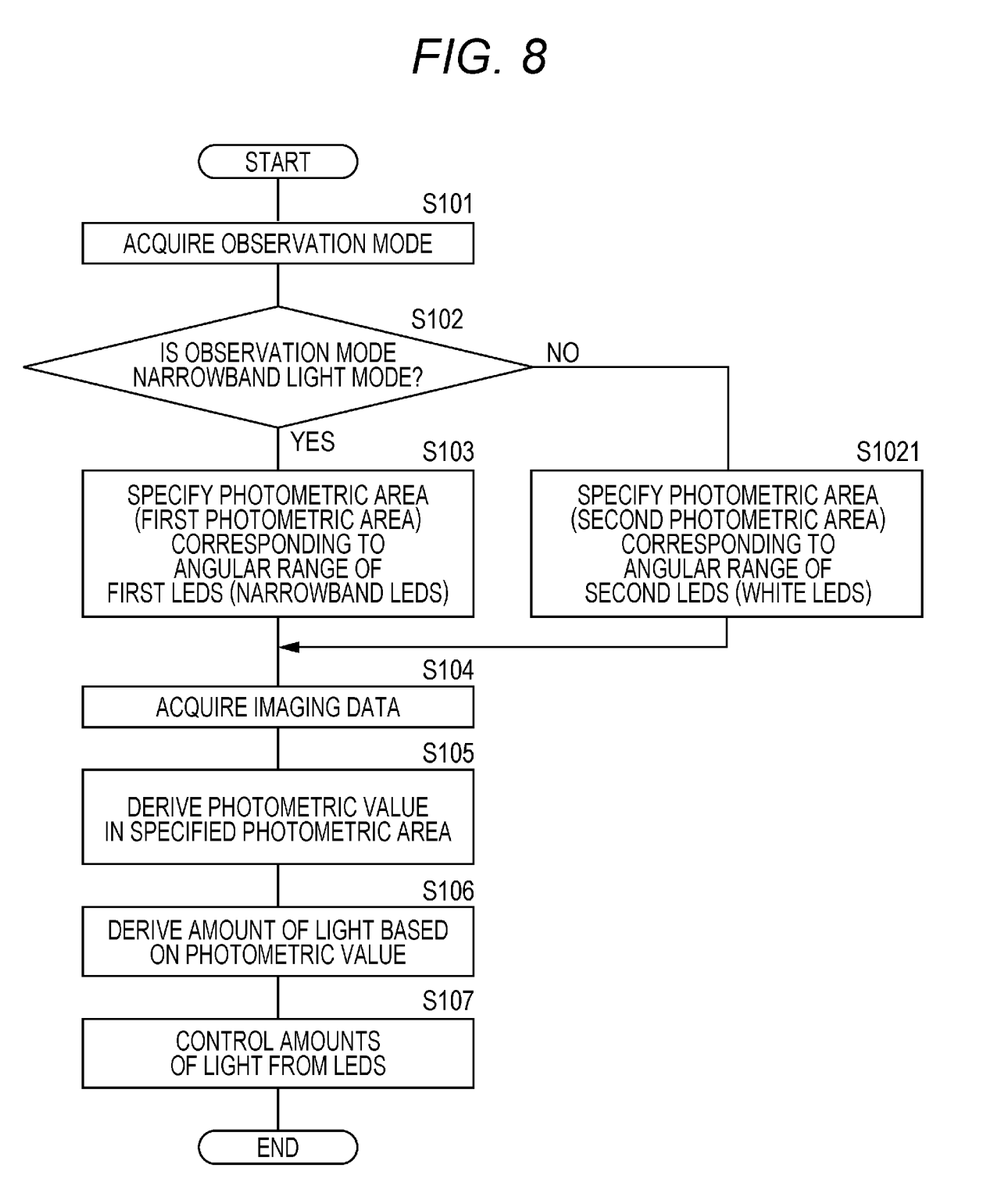
FIG. 8 is a flowchart illustrating an example of a processing procedure performed by a light amount control unit of the endoscope.

FIG. 8 is a flowchart illustrating an example of a processing procedure performed by the light amount control unit 8 of the endoscope 1. The light amount control unit 8 of the endoscope 1 starts the processing according to the flowchart in response to an operator's operation, for example, using the operation button 31.

The light amount control unit 8 acquires an observation mode (S101). For example, the light amount control unit 8 acquires a control command given from the control unit 11 of the processor device 10. The control command is a command for controlling the illumination drive unit 73, including information regarding an observation mode.

The light amount control unit 8 determines whether or not the observation mode is a narrowband light mode (S102). The light amount control unit 8 specifies whether the observation mode is a white mode using the second LEDs 72 (white LEDs) or a narrowband mode using the first LEDs 71 (narrowband LEDs) based on the control command acquired from the control unit 11 of the processor device 10.

When the observation mode is a narrowband light mode (S102: YES), the light amount control unit 8 specifies a photometric area (first photometric area) corresponding to an angular range of the first LEDs 71 (narrowband LEDs). The light amount control unit 8 specifies the photometric area (first photometric area) corresponding the angular range of the first LEDs 71 (narrowband LEDs), for example, by referring to a memory in the microcomputer or the like constituting the light amount control unit 8 (S103).

When the observation mode is not a narrowband light mode (S102: NO), that is, when the observation mode is a white light mode, the light amount control unit 8 specifies a photometric area (second photometric area) corresponding to an angular range of the second LEDs 72 (white LEDs). The light amount control unit 8 specifies the photometric area (second photometric area) corresponding the angular range of the second LEDs 72 (white LEDs), for example, by referring to a memory in the microcomputer or the like constituting the light amount control unit 8 (S1021). In specifying the first photometric area and the second photometric area, area information regarding these photometric areas (first photometric area and second photometric area) is defined according to, for example, a range based on image coordinate system, a range based on pixel number, or the like in an image captured by the imaging unit 6.

The light amount control unit 8 acquires imaging data output from the imaging unit 6 (S104). The light amount control unit 8 acquires imaging data (image signal) output from the imaging unit 6 via the reception circuit 61 and the gain circuit 62 that perform preprocessing, for example, AD conversion or white balance correction.

The light amount control unit 8 derives a photometric value in the specified photometric area from the acquired imaging data (S105). From the imaging data (image signal) acquired from the imaging unit 6, the light amount control unit 8 derives a photometric value in either the photometric area (first photometric area) corresponding to the angular range of the first LEDs 71 (narrowband LEDs) or the photometric area (second photometric area) corresponding to the angular range of the second LED 72 (white LED) specified according to the observation mode. When the observation mode is a white mode, the light amount control unit 8 derives a photometric value in the photometric area (second photometric area) of the second LEDs 72 (white LEDs). When the observation mode is a narrowband mode, the light amount control unit 8 derives a photometric value in the photometric area (first photometric area) of the first LEDs 71 (narrowband LEDs). The light amount control unit 8 derives a photometric value by using the photometric circuit 81 constituting the light amount control unit 8. The photometric value may derive an average value (average photometric value) or a largest value (peak photometric value) of photometric values in the entire photometric area (first photometric area or second photometric area). As described above, each of the photometric area (first photometric area) corresponding to the angular range of the first LEDs 71 (narrowband LEDs) and the photometric area (second photometric area) corresponding to the angular range of the second LEDs 72 (white LEDs) are segmented into a plurality of areas, for example, four areas (Areas 1 to 4) based on vertical and horizontal directions. In a case where the photometric area is segmented as described above, the light amount control unit 8 derives photometric values for the respective segments, that is, four photometric values including a photometric value in an upper right photometric area (Area 1), a photometric value in a lower right photometric area (Area 4), a photometric value in a lower left photometric area (Area 3), and a photometric value in an upper left photometric area (Area 2), according to each observation mode (white mode or narrowband mode). Therefore, the light amount control unit 8 may derive a photometric value for each segment (for each of the plurality of segmented areas) in each observation mode (white mode or narrowband mode).

The light amount control unit 8 derives an amount of light based on the derived photometric value (S106). The light amount control unit 8 derives the amount of light based on the photometric value, for example, by referring to a lookup table stored in a memory of the microcomputer or the like constituting the light amount control unit 8. The light amount control unit 8 may derive an amount of light for each segment based on the photometric value derived for each segment (for each of the plurality of segmented areas).

The light amount control unit 8 controls amounts of light from the LEDs based on the derived amount of light (S107). The light amount control unit 8 controls the amounts of light from the LEDs (first LEDs 71 (narrowband LEDs) and second LEDs 72 (white LEDs)) of the illumination unit 7 by outputting, for example, LED current values to the light amount control circuit 83 as the information regarding the derived amount of light. The light amount control unit 8 may control amounts of light from the LEDs (first LEDs 71 and second LEDs 72) for each segment based on the amount of light derived for each segment (for each of the plurality of segmented areas). Since the individual LEDs including the first LEDs 71 (narrowband LEDs) and the second LEDs 72

(white LEDs) are arranged in respectively corresponding ones of the plurality of segmented areas, the amounts of light from these individual LEDs (first LEDs 71 and second LEDs 72) can be controlled based on the photometric value for each of the plurality of segmented areas.

According to the present embodiment, the light amount control unit 8 of the endoscope 1 derives a photometric value at an observation spot in a body part such as a body cavity based on imaging data (image signal) from the imaging unit 6, and derives an amount of light for each of the first light output unit and the second light output unit based on the derived photometric value. Since an area of an observation spot for which a photometric value is to be derived is an area (photometric area) corresponding to each of the angular ranges (light distribution ranges) of the first light output unit and the second light output unit, an amount of light in the area can be derived according to the angular ranges (light distribution ranges) of the first light output unit and the second light output unit. The light amount control unit 8 controls the first light output unit and the second light output unit based on the respective derived amounts of light to cause the first light output unit and the second light output unit to output illumination light according to the respective derived amounts of light. Therefore, it is possible to efficiently perform dimming according to each of the photometric values of illumination light in different wavelength ranges.

According to the present embodiment, the angular range (light distribution range) of the second light output unit is larger than the angular range of the first light output unit. Therefore, regarding an area (photometric area) for which an amount of light is to be derived by the light amount control unit 8, an area of an observation spot corresponding to the angular range of the first light output unit is set to be narrower than an area of an observation spot corresponding to the angular range of the second light output unit, such that the photometric values according to the light distribution characteristics of the first light output unit and the second light output unit can be derived, thereby improving the accuracy of each of the photometric values.

According to the present embodiment, an observation spot imaged by the imaging unit 6 is segmented into a plurality of areas, and a plurality of first light output units and a plurality of second light output units are arranged in respectively corresponding ones of the plurality of areas. Since the light amount control unit 8 derives amounts of light from the first light output unit and the second light output unit based on a photometric value in each of the plurality of areas, it is possible to acquire a suitable image (endoscopic image) corresponding to the first light output unit and the second light output unit in each of the plurality of areas.

Second Embodiment

Figure 9:
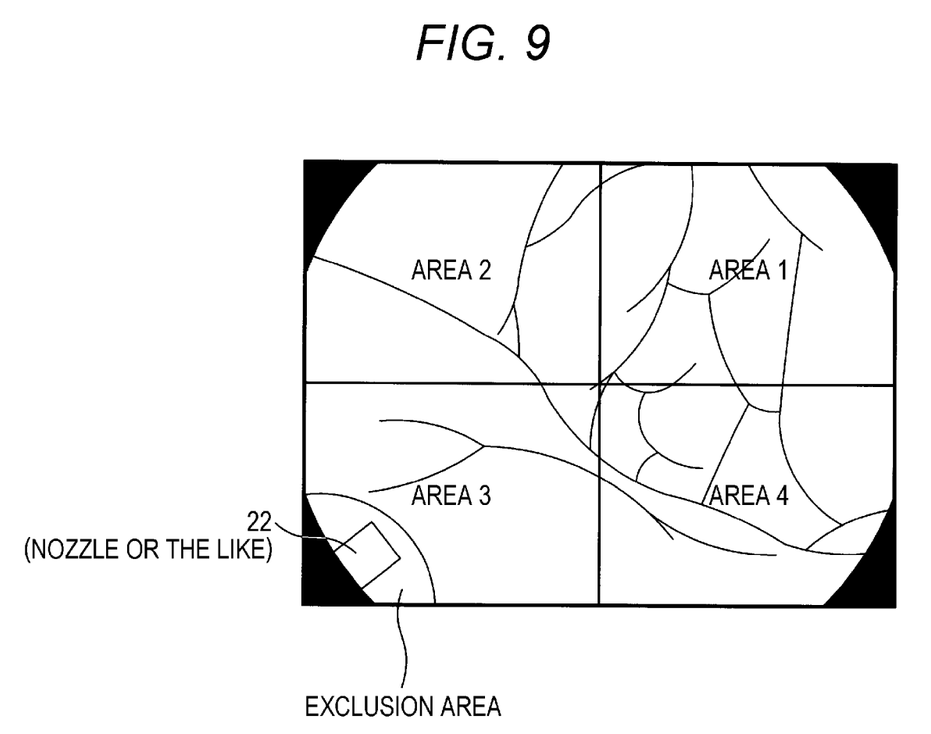
FIG. 9 is an explanatory diagram illustrating an observation spot (photometric area) when illuminated by a second light output unit (white LEDs) according to a second embodiment.

FIG. 9 is an explanatory diagram illustrating an observation spot (photometric area) when illuminated by the second light output unit (white LEDs) according to a second embodiment. As illustrated in the present embodiment, in a certain model of the endoscope 1, when an observation spot is illuminated by the second light output unit (white LEDs), the observation spot (photometric area) may include a part such as a nozzle in the distal tip 22 or a portion further protruding from the distal tip 22, for example, at a predetermined position such as a lower left position of the observation spot (photometric area).

In this case, in particular, when a part made of metal having a high reflectance such as a nozzle is included in the photometric area, halation may occur locally, making it difficult to appropriately derive a photometric value in the photometric area. In such a model of the endoscope 1 as described above, it is possible to appropriately derive a photometric value, for example, by setting a position of a part included and imaged in a certain position on the screen, such as a nozzle, as an exclusion area in advance, and setting the photometric area (remaining area) excluding the exclusion area as a target.

Figure 10:
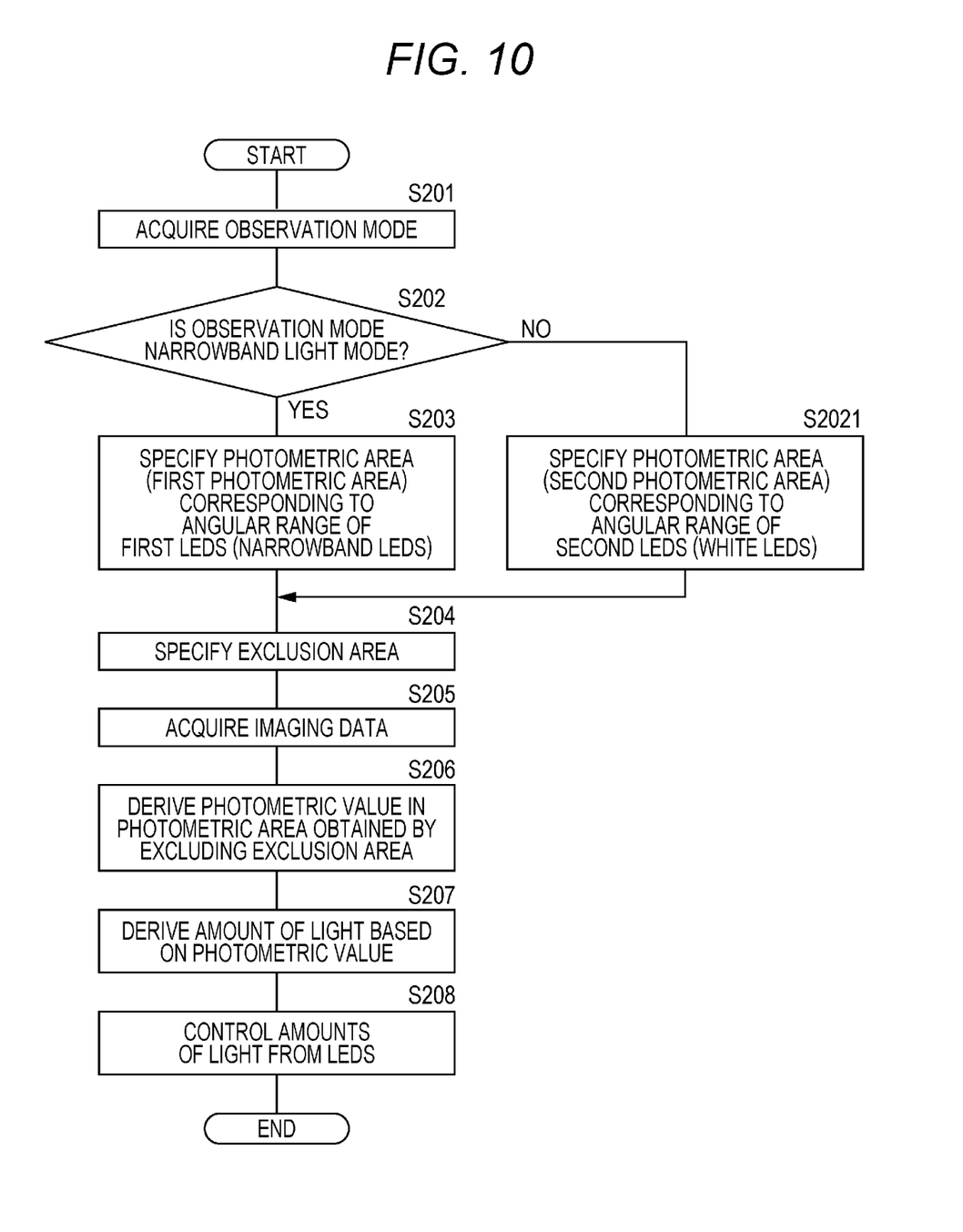
FIG. 10 is a flowchart illustrating an example of a processing procedure performed by a light amount control unit of the endoscope.

FIG. 10 is a flowchart illustrating an example of a processing procedure performed by the light amount control unit 8 of the endoscope 1. The light amount control unit 8 of the endoscope 1 starts the processing according to the flowchart in response to an operator's operation, for example, using the operation button 31.

The light amount control unit 8 acquires an observation mode (S201). The light amount control unit 8 determines whether or not the observation mode is a narrowband light mode (S202). When the observation mode is a narrowband light mode (S202:YES), the light amount control unit 8 specifies a photometric area (first photometric area) corresponding to an angular range of the first LEDs 71 (narrowband LEDs) (S203). When the observation mode is not a narrowband light mode (S202:NO), that is, when the observation mode is a white light mode, the light amount control unit 8 specifies a photometric area (second photometric area) corresponding to an angular range of the second LEDs 72 (white LEDs) (S2021). The light amount control unit 8 performs the processing from S201 to S2021 and S203 similarly to S101 to S1021 and S103 in the first embodiment.

The light amount control unit 8 specifies an exclusion area (S204). The light amount control unit 8 specifies the exclusion area by referring to a memory of the microcomputer or the like constituting the light amount control unit 8. The exclusion area may be an area common to observation modes, or may be an area different between these observation modes. The area information regarding the exclusion area may be defined according to a range based on image coordinate system, a range based on pixel number, or the like in an image captured by the imaging unit 6.

The light amount control unit 8 acquires imaging data output from the imaging unit 6 (S205). The light amount control unit 8 performs the processing of S205 similarly to S104 in the first embodiment.

The light amount control unit 8 derives a photometric value in a photometric area obtained by excluding the exclusion area from the acquired imaging data (S206). When deriving the photometric value in the photometric area (first photometric area or second photometric area) specified according to the observation mode similarly to S105 in the first embodiment, the light amount control unit 8 derives a photometric value in a photometric area (remaining area) obtained by excluding the exclusion area from the photometric area.

The light amount control unit 8 derives an amount of light based on the derived photometric value (S207). The light amount control unit 8 controls amounts of light from the LEDs based on the derived amount of light (S208). The light amount control unit 8 performs the processing of S207 and S208 similarly to S106 and S107 in the first embodiment.

According to the present embodiment, when an exclusion region is set in any area (photometric area), the light amount control unit 8 derives a photometric value in an area (remaining area) obtained by excluding the exclusion region.

The area information regarding the exclusion region is stored, for example, in a storage area accessible from the light amount control unit 8, such as a RAM built in the light amount control unit 8, and the light amount control unit 8 can acquire the area information regarding the exclusion region by referring to the RAM or the like. The exclusion region is set, for example, to correspond to a predetermined area of a captured image in which a nozzle or the like provided in the distal tip 22 is normally included. That is, the nozzle and the like is always included in the predetermined area of the captured image corresponding to the exclusion region. Since the nozzle has a relatively high reflectance, it is highly likely that halation occurs due to excessive reflection of illumination light. In this regard, in a case where an exclusion region is set in any of the plurality of areas, the light amount control unit 8 derives an amount of light from each of the first light output unit and the second light output unit based on the photometric value in an area (remaining area) obtained by excluding the exclusion region from the area in which the exclusion region is set. Therefore, even when halation occurs locally due to reflection by the nozzle or the like, it is possible to appropriately derive an amount of light from each of the first light output unit and the second light output unit to control the first light output unit and the second light output unit.

It should be noted that the embodiments disclosed herein are illustrative in all respects and are not restrictive. The technical features described in the embodiments can be combined with each other, and the scope of the present invention is intended to include all modifications and equivalents within the scope of the claims.

REFERENCE SIGNS LIST

1 Endoscope
2 Insertion tube
20 Soft portion
21 Bending section
22 Distal tip
23 Connection portion
24 Housing
25 Objective lens
26 Light distribution lens
3 Operation unit
30 Bending operation knob
31 Operation button
4 Universal tube
5 Connector unit
6 Imaging unit
60 Imaging drive unit
61 Reception circuit
62 Gain circuit
7 Illumination unit
70 Substrate
71 First LED (first light emitting element, narrowband LED)
72 Second LED (second light emitting element, white LED)
73 Illumination drive unit
8 Light amount control unit
81 Photometric circuit
82 Automatic dimming control unit
83 Light amount control circuit
10 Processor device
11 Control unit
12 Signal processing circuit
13 Additional processing circuit
14 Monitor
15 Freeze processing unit

The invention claimed is:

1. An endoscope comprising:
an imaging unit provided in a distal tip of an insertion tube to image an observation spot via an objective lens;
a first light output unit disposed around the objective lens to output first illumination light for illuminating the observation spot;
a second light output unit disposed around the objective lens to output second illumination light for illuminating the observation spot in a wavelength range wider than that of the first illumination light in an angular range larger than that of the first light output unit; and
a light amount control unit controlling an amount of light output from each of the first light output unit and the second light output unit,
wherein the light amount control unit:
derives a photometric value in an area of the observation spot corresponding to each of the angular ranges of the first light output unit and the second light output unit based on imaging data about the observation spot output from the imaging unit;
derives the amount of light from each of the first light output unit and the second light output unit based on the derived photometric value; and
causes each of the first light output unit and the second light output unit to output illumination light based on the derived amount of light.

2. The endoscope according to claim 1,
wherein the area of the observation spot corresponding to the angular range of the first light output unit for which the photometric value is derived by the light amount control unit is narrower than the area of the observation spot corresponding to the angular range of the second light output unit for which the photometric value is derived by the light amount control unit.

3. The endoscope according to claim 1, wherein the imaging data includes first imaging data about the observation spot illuminated by the first illumination light and second imaging data about the observation spot illuminated by the second illumination light,
the photometric values include a first photometric value derived based on the first imaging data and a second photometric value derived based on the second imaging data, and
the light amount control unit;
derives an amount of light from the first light output unit based on the first photometric value, and
derives an amount of light from the second light output unit based on the second photometric value.

4. The endoscope according to claim 1, wherein the observation spot imaged by the imaging unit includes a plurality of segmented areas,
a plurality of first light output units and a plurality of second light output units are provided to correspond to the plurality of areas,
the light amount control unit derives a photometric value in each of the plurality of areas,
the light amount control unit derives an amount of light from each of the first light output unit and the second light output unit corresponding to each of the plurality of areas based on the derived photometric value, and
the light amount control unit causes each of the first light output units and the second light output units to output illumination light based on the derived amount of light.

5. The endoscope according to claim 1, wherein when an exclusion region is set in the area of the observation spot, the light amount control unit derives a photometric value in an area obtained by excluding the exclusion region.

6. The endoscope according to claim 1, wherein the angular range of the second illumination light from the second light output unit is equal to or larger than a viewing angle of the imaging unit.

7. The endoscope according to claim 1, wherein the imaging unit has a viewing angle of 180° or more.

8. The endoscope according to claim 1, wherein the first illumination light is narrowband light, and the second illumination light is white light.

9. A non-transitory computer readable medium containing a program for causing a computer to execute the following processing, the computer controlling an amount of light output from each of a first light output unit disposed around an objective lens to output first illumination light for illuminating an observation spot, and a second light output unit disposed around the objective lens to output second illumination light for illuminating the observation spot in a wavelength range wider than that of the first illumination light in an angular range larger than that of the first light output unit:

deriving a photometric value in an area of the observation spot corresponding to an angular range of each of the first light output unit and the second light output unit based on imaging data about the observation spot output from an imaging unit imaging the observation spot via the objective lens;

deriving the amount of light from each of the first light output unit and the second light output unit based on the derived photometric value; and causing each of the first light output unit and the second light output unit to output illumination light based on the derived amount of light.

10. An information processing method performed by a computer controlling an amount of light output from each of a first light output unit disposed around an objective lens to output first illumination light for illuminating an observation spot, and a second light output unit disposed around the objective lens to output second illumination light for illuminating the observation spot in a wavelength range wider than that of the first illumination light in an angular range larger than that of the first light output unit, the information processing method comprising:

deriving a photometric value in an area of the observation spot corresponding to an angular range of each of the first light output unit and the second light output unit based on imaging data about the observation spot output from an imaging unit imaging the observation spot via the objective lens;

deriving the amount of light from each of the first light output unit and the second light output unit based on the derived photometric value; and causing each of the first light output unit and the second light output unit to output illumination light based on the derived amount of light.

* * * * *